United States Patent
Arumugam et al.

(10) Patent No.: US 11,617,721 B2
(45) Date of Patent: Apr. 4, 2023

(54) SOLID PHARMACEUTICAL DOSAGE FORMS OF VITAMIN K 1 AND PROCESS OF PREPARATION THEREOF

(71) Applicant: ATOZ PHARMACEUTICALS PVT LTD, Chennai (IN)

(72) Inventors: Olaganathan Arumugam, Chennai (IN); Natarajan Venkatachalam, Chennai (IN)

(73) Assignee: ATOZ PHARMACEUTICALS LTD., Chennai (IN)

( * ) Notice: Subject to any disclaimer, the term of this patent is extended or adjusted under 35 U.S.C. 154(b) by 0 days.

(21) Appl. No.: 16/722,614

(22) Filed: Dec. 20, 2019

(65) Prior Publication Data

US 2021/0121407 A1  Apr. 29, 2021

(30) Foreign Application Priority Data

Oct. 23, 2019  (IN) .............. 201941043002

(51) Int. Cl.
- *A61K 9/20* (2006.01)
- *A61K 9/16* (2006.01)
- *A61K 9/28* (2006.01)
- *A61K 31/122* (2006.01)

(52) U.S. Cl.
CPC .............. *A61K 9/2095* (2013.01); *A61K 9/16* (2013.01); *A61K 9/2018* (2013.01); *A61K 9/2054* (2013.01); *A61K 9/2059* (2013.01); *A61K 9/28* (2013.01); *A61K 31/122* (2013.01)

(58) Field of Classification Search
None
See application file for complete search history.

(56) References Cited

U.S. PATENT DOCUMENTS

| | | | |
|---|---|---|---|
| 2005/0013857 A1* | 1/2005 | Fu | A61K 9/0056 424/464 |
| 2018/0177735 A1* | 6/2018 | Gajjar | A61K 31/122 |

OTHER PUBLICATIONS

Hartesi et al., Starch as Pharmaceutical Excipient, Int. J. Pharm. Sci. Rev. Res., 41(2), Nov.-Dec. Article No. 14, pp. 59-64 (Year: 2016).*

* cited by examiner

*Primary Examiner* — Isis A Ghali

(57) ABSTRACT

The present disclosure relates to a dry process for preparing a solid pharmaceutical dosage form of vitamin K1 comprising: a) blending vitamin K1 with a first diluent under a first set of pre-determined conditions to obtain a first mixture; b) contacting the first mixture with a second diluent under a second set of pre-determined conditions to obtain a second mixture; c) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1.

6 Claims, No Drawings

SOLID PHARMACEUTICAL DOSAGE FORMS OF VITAMIN K 1 AND PROCESS OF PREPARATION THEREOF

FIELD OF THE INVENTION

The present invention relates to the field of pharmaceutical formulations, and in particular relates to solid pharmaceutical dosage forms of vitamin K1. The present disclosure also provides for a convenient process of preparation of the solid pharmaceutical dosage forms of vitamin K1. The present application is based on, and claims priority from an Indian Application Number 201941043002 filed on 23 Oct. 2019, the disclosure of which is hereby incorporated by reference herein

BACKGROUND OF THE INVENTION

Phylloquinone is often called vitamin K1 or Phytonadione. It is a fat-soluble vitamin that is stable to air and moisture but decomposes in sunlight. It is found naturally in a wide variety of green plants. These substances were found to be essential for synthesizing prothrombin in the liver, which is a precursor of the enzyme thrombin causing blood coagulation reaction and were also known to prevent release of calcium from the bones.

Conventionally, vitamin K1 is administered as solid oral dosage forms and injectable forms. The Vitamin K1 has eight diastereomers due to the existence of two geometrical isomers (E and Z) and two asymmetric carbon atoms. Among the eight diastereoisomers only the trans phytonadione (2',3'-trans-7R,11R-stereoisomer) is vitamin and other seven isomeric forms of phytonadione are non-vitamin. The synthetic or commercially available dosage forms of vitamin K1 is a mixture of trans (E) and cis (Z) isomers, having limits of not less than 75% of trans phytonadione, and not more than 21% of cis phytonadione. Other than eight diastereomers, the synthetic or commercially available dosage forms of vitamin K1 has also an isomeric by-product trans epoxy phytonadione (isomer) and its limit is not more than 4%.

Some of the well-known injectable formulations of vitamin K1 are Mephyton, Aquamephyton, Vitamin K1, and phytonadione. WO2016038626 discloses an injectable composition of Vitamin K1 for parenteral administration comprising Vitamin K1 and pharmaceutically acceptable excipients, wherein the amount of 2-methyl-3-[(2E,7R, 1 1R)-3, 7,1 1,15-tetramethyl-2-hexadecenyl]-1,4-naphthalenedione (trans isomer) is at least 50% by weight of active ingredient.

Solid pharmaceutical dosage forms of vitamin K1 are being increasingly developed to overcome the challenges associated with administering injectable forms of vitamin K1. For example, U.S. Pat. No. 4,892,889 discloses a process for making a directly-compressible vitamin powder utilizes a conventional spray-dryer. The resulting powder is comprised of a fat-soluble vitamin, a water-soluble carbohydrate, and a gelatin having a bloom number between 30 and 300. US 20180177735 discloses a process of preparing a stable pharmaceutical composition of phytonadione comprising: (a) preparing a dispersion of phytonadione in a pharmaceutically acceptable binder; (b) mixing or spraying the dispersion with one or more pharmaceutically acceptable excipients to form the stable pharmaceutical composition; and (c) formulating the stable pharmaceutical composition obtained from step (b) into a pharmaceutically administrable dosage form. However, most of these processes in development of solid oral dosage forms of vitamin K1 are based on utilizing aqueous or non-aqueous solvents and drying steps which incurs energy, time and cost. Also, formulations prepared by wet methods often show incremental hardness as a function of time and storage temperature; and hence are more likely to show variable product performance.

Also, conventionally used formulations involve the use of phosphate-based fillers such as, dicalcium phosphate (DCP). Although known to provide good flowability and good compactibility, DCP is insoluble and can be very abrasive, which could cause reduced tooling life due to wear on the equipment during tablet manufacture. High levels of lubricants are required to overcome the abrasiveness, but elevated levels of hydrophobic lubricants can impact the mechanical strength of the tablets and disintegration/dissolution performance.

The above information is presented as background information only to help the reader to understand the present invention. Applicants have made no determination and make no assertion as to whether any of the above might be applicable as prior art with regard to the present application.

OBJECT OF THE INVENTION

The principal object of the embodiments herein is to provide for a solid pharmaceutical dosage form of vitamin K1.

Another object of the present invention is to provide for a simple and convenient dry process of preparation of solid oral dosage forms of vitamin K1.

Yet another object of the invention is to provide for a dicalcium phosphate-free solid dosage form of vitamin K1.

SUMMARY OF THE INVENTION

Accordingly, the invention provides a pharmaceutical formulation comprising: i) vitamin K1 having a weight percentage in a range of 1-10% with respect to the composition; ii) at least one diluent having a weight percentage in a range of 20-85% with respect to the composition; and iii) at least one disintegrant having a weight percentage in a range of 5-20% with respect to the composition, iv) at least one lubricant having a weight percentage in a range of 1-2% with respect to the composition, v) at least one glidant having a weight percentage in a range of 1-5% with respect to the composition, wherein said composition is substantially free of phosphates.

In another aspect of the present disclosure, there is provided a dry process for preparation of pharmaceutical dosage form of vitamin K1 comprising: i) vitamin K1 having a weight percentage in a range of 1-10% with respect to the composition; ii) at least one diluent having a weight percentage in a range of 20-85% with respect to the composition; and iii) at least one disintegrant having a weight percentage in a range of 5-20% with respect to the composition, iv) at least one lubricant having a weight percentage in a range of 1-2% with respect to the composition, v) at least one glidant having a weight percentage in a range of 1-5% with respect to the composition, wherein said composition is substantially free of phosphates, said process comprising: a) blending vitamin K1 with a first diluent under a first set of pre-determined conditions to obtain a first mixture; b) contacting the first mixture with a second diluent under a second set of pre-determined conditions to obtain a second mixture; c) mixing the second mixture with the excipients selected from a group consisting of disintegrant, lubricant and glidant, under a third set of pre-determined conditions to obtain a third mixture; and d) compressing or encapsulating the third mixture to obtain the solid pharmaceutical dosage form of vitamin K1.

In another aspect of the present disclosure, there is provided a stable vitamin K1 dosage form comprising trans phytonadione having a weight percentage in a range of 80-98% with respect to the total eight diastereomers; cis phytonadione having a weight percentage in the range of 1-21% with respect to the total eight diastereomers, wherein the dosage form is substantially free (i.e. each isomer: NMT 0.15% w/w) of other six diastereomers of vitamin K1.

These and other aspects of the embodiments herein will be better appreciated and understood when considered in conjunction with the following description. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF INVENTION

The embodiments herein and the various features and advantageous details thereof are explained more fully with reference to the non-limiting embodiments that are illustrated in the accompanying tables and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

Conventionally used solid dosage forms of vitamin K1 largely contain phosphate-based excipients, such as dicalcium phosphate (DCP) to impart good flowability and compactibility. However, usage of DCP could cause reduced tooling life due to wear on the equipment during tablet manufacture. To overcome these problems, high levels of lubricants are added to overcome the abrasiveness, but elevated levels of hydrophobic lubricants can impact the mechanical strength of the tablets and disintegration/dissolution performance. Also, conventional processes to prepare the solid dosage forms of vitamin K1 are based on utilizing wet granulation technique, which incur several process steps and impose huge costs on the time and energy. Therefore, the object of the present disclosure is to provide for a DCP-free formulations of vitamin K1 through a simple, cost-effective, energy-effective, solvent free (both aqueous and organic), dry process.

In an embodiment of the present disclosure, there is provided a solid pharmaceutical dosage form of vitamin K1 comprising: a) vitamin K1 having a weight percentage in a range of 1-10% with respect to the composition; b) at least one diluent having a weight percentage in a range of 20-85% with respect to the composition; and c) at least one disintegrant having a weight percentage in a range of 5-20% with respect to the composition, d) at least one lubricant having a weight percentage in a range of 1-2% with respect to the composition, e) at least one glidant having a weight percentage in a range of 1-5% with respect to the composition, wherein said composition is substantially free of phosphates.

In another embodiment of the present disclosure, there is provided a solid pharmaceutical dosage form of vitamin K1 comprising a) vitamin K1 having a weight percentage of 3.7% with respect to the composition; b) microcrystalline cellulose having a weight percentage of 24.7% with respect to the composition; c) lactose monohydrate having a weight percentage of 57.66% with respect to the composition; d) pre-gelatinized starch having a weight percentage of 10% with respect to the composition; e) colloidal silicon dioxide having a weight percentage of 2.78% with respect to the composition; and f) magnesium stearate having a weight percentage of 1.16% with respect to the composition.

In an embodiment of the present disclosure, there is provided a solid pharmaceutical dosage form of vitamin K1 as described herein, wherein the vitamin K1 to the at least one disintegrant w/w ratio in a range of 1:2.5 to 1:6.

In an embodiment of the present disclosure, there is provided a solid pharmaceutical dosage form of vitamin K1 comprising: a) vitamin K1 having a weight percentage in a range of 1-10% with respect to the composition; b) at least one diluent having a weight percentage in a range of 20-85% with respect to the composition; and c) at least one disintegrant having a weight percentage in a range of 5-20% with respect to the composition, d) at least one lubricant having a weight percentage in a range of 1-2% with respect to the composition, e) at least one glidant having a weight percentage in a range of 1-5% with respect to the composition, and wherein the vitamin K1 to the at least one disintegrant w/w ratio in a range of 1:2.5 to 1:6, and wherein said composition is substantially free of phosphates.

In an embodiment of the present disclosure, there is provided a solid pharmaceutical dosage form of vitamin K1 as described herein, wherein the diluent is selected from a group consisting of microcrystalline cellulose (MCC), silicified MCC, microfine cellulose, lactose monohydrate, lactose anhydrous, mannitol, and co-processed or combinations thereof; the disintegrant(s) is at least one selected from a group consisting of starch, pre-gelatinized starch, partially pre-gelatinized starch, crospovidone, sodium starch glycolate, croscarmellose sodium, and hydroxypropyl cellulose; the lubricant(s) is at least one selected from a group consisting of magnesium stearate, calcium stearate, talc and sodium stearyl fumarate; and the glidant(s) is at least one of silicon dioxide, talc and colloidal silicon dioxide. In another embodiment of the present disclosure, at least one diluent is a coprocessed or combinations of microcrystalline cellulose (MCC), and lactose monohydrate or microcrystalline cellulose (MCC), and lactose anhydrous or microcrystalline cellulose (MCC), and mannitol; the disintegrant(s) is pre-gelatinized starch; the lubricant(s) is magnesium stearate; and the glidant(s) is colloidal silicon dioxide.

In an embodiment of the present disclosure, there is provided a solid pharmaceutical dosage form of vitamin K1 comprising: a) Vitamin K1 having a weight percentage in a range of 1-10% with respect to the composition; b) at least one diluent having a weight percentage in a range of 20-85% with respect to the composition; and c) at least one disintegrant having a weight percentage in a range of 5-20% with respect to the composition, d) at least one lubricant having a weight percentage in a range of 1-2% with respect to the composition, e) at least one glidant having a weight percentage in a range of 1-5% with respect to the composition, and wherein said composition is substantially free of phosphates, and wherein the diluent is selected from a group consisting of microcrystalline cellulose (MCC), silicified MCC, microfine cellulose, lactose monohydrate, lactose anhydrous, mannitol, and coprocessed or combinations thereof; the disintegrant(s) is at least one selected from a group consisting of starch, pre-gelatinized starch, partially pre-gelatinized starch, crospovidone, sodium starch glycolate, croscarmellose sodium, and hydroxypropyl cellulose; the lubricant(s) is at least one selected from a group consisting of magnesium stearate, calcium stearate, talc, and sodium stearyl fumarate; and the glidant(s) is at least one of silicon dioxide, talc and colloidal silicon dioxide.

In an embodiment of the present disclosure, there is provided a dry process for preparation of pharmaceutical dosage form of vitamin K1 comprising: a) blending vitamin K1 with a first diluent under a first set of pre-determined conditions to obtain a first mixture; b) contacting the first mixture with a second diluent under a second set of pre-determined conditions to obtain a second mixture; c) mixing the second mixture with the excipients selected from a group consisting of disintegrant, lubricant and glidant etc under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 comprising: a) vitamin K1 having a weight percentage in a range of 1-10% with respect to the composition; b) at least one diluent having a weight percentage in a range of 20-85% with respect to the composition; and c) at least one disintegrant having a weight percentage in a range of 5-20% with respect to the composition, d) at least one lubricant having a weight percentage in a range of 1-2% with respect to the composition, e) at least one glidant having a weight percentage in a range of 1-5% with respect to the composition, wherein said composition is substantially free of phosphates, said process comprising: a) blending vitamin K1 with a first diluent under a first set of pre-determined conditions to obtain a first mixture; b) contacting the first mixture with a second diluent under a second set of pre-determined conditions to obtain a second mixture; c) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the first set of pre-determined conditions include mixing for a period of 5-15 minutes at a speed of 200-350 rpm using high shear mixers; the second set of pre-determined conditions include mixing for a period of 5-15 minutes at a speed of 10-20 rpm; and the third set of pre-determined conditions include mixing for a period of 5-15 minutes at a speed of 10-20 rpm; and wherein the process is carried out at a temperature range of 15-30° C., and a relative humidity limit of not more than (NMT) 65%. In another embodiment, the relative humidity limit is in a range of 40-65%.

In an embodiment of the present disclosure, there is provided a dry process for preparation of pharmaceutical dosage form of vitamin K1 comprising: a) blending vitamin K1 with a first diluent under a first set of pre-determined conditions to obtain a first mixture; b) contacting the first mixture with a second diluent under a second set of pre-determined conditions to obtain a second mixture; c) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1, wherein the first set of pre-determined conditions include mixing for a period of 5-15 minutes at a speed of 200-350 rpm using high shear mixers; the second set of pre-determined conditions include mixing for a period of 5-15 minutes at a speed of 10-20 rpm; and the third set of pre-determined conditions include mixing for a period of 5-15 minutes at a speed of 10-20 rpm; and wherein the process is carried out at a temperature range of 15-30° C., and a relative humidity limit of NMT 65%. In another embodiment, the relative humidity limit is in a range of 40-65%.

In an embodiment of the present disclosure, there is provided a dry process for preparation of pharmaceutical dosage form of vitamin K1 as described herein, wherein the vitamin K1 to the diluent weight ratio is in the range of 1:1 to 1:100. In another embodiment, the vitamin K1 to the diluent weight ratio is in the range of 1:1 to 1:15.

In an embodiment of the present disclosure, there is provided a dry process for preparation of pharmaceutical dosage form of vitamin K1 comprising: a) blending vitamin K1 with a first diluent at a weight ratio in the range of 1:1 to 1:100 under a first set of pre-determined conditions to obtain a first mixture; b) contacting the first mixture with a second diluent under a second set of pre-determined conditions to obtain a second mixture; c) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the diluent comprises a first diluent and a second diluent, wherein the first diluent and the second diluent include at least one selected from a group consisting of microcrystalline cellulose (MCC), silicified MCC, microfine cellulose, lactose monohydrate, lactose anhydrous mannitol, and coprocessed or combinations thereof.

In an embodiment of the present disclosure, there is provided a dry process for preparation of pharmaceutical dosage form of vitamin K1 comprising: a) blending vitamin K1 with a first diluent at under a first set of pre-determined conditions to obtain a first mixture; b) contacting the first mixture with a second diluent under a second set of pre-determined conditions to obtain a second mixture, wherein the first diluent and the second diluent include at least one selected from a group consisting of microcrystalline cellulose (MCC), silicified MCC, microfine cellulose, lactose monohydrate, lactose anhydrous, mannitol, and combinations thereof; c) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the first diluent and the second diluent may be same or different or it may be co-processed or combination of two or more excipients.

In an embodiment of the present disclosure, there is provided a dry process for preparation of pharmaceutical dosage form of vitamin K1 comprising: a) blending vitamin K1 with a first diluent at under a first set of pre-determined conditions to obtain a first mixture; b) contacting the first mixture with a second diluent under a second set of pre-determined conditions to obtain a second mixture, wherein the first diluent and the second diluent include at least one selected from a group consisting of microcrystalline cellulose (MCC), silicified MCC, microfine cellulose, lactose monohydrate, lactose anhydrous, mannitol, and coprocessed or combinations thereof, and wherein the first diluent and the second diluent may be same or different; c) mixing the second mixture with the excipients selected from the group consisting of disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the first diluent is microcrystalline cellulose, and wherein the second diluent is lactose monohydrate.

In an embodiment of the present disclosure, there is provided a dry process for preparation of pharmaceutical dosage form of vitamin K1 comprising: a) blending vitamin K1 with a first diluent at under a first set of pre-determined conditions to obtain a first mixture; b) contacting the first mixture with a second diluent under a second set of pre-determined conditions to obtain a second mixture, wherein the first diluent is microcrystalline cellulose, and wherein the second diluent is lactose monohydrate; c) mixing the second mixture with the excipients selected from the group consisting of disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the lactose monohydrate has a particle size in the range of 50 µm-600 µm.

In an embodiment of the present disclosure, there is provided a dry process for preparation of pharmaceutical dosage form of vitamin K1 comprising: a) blending vitamin K1 with a first diluent at under a first set of pre-determined conditions to obtain a first mixture; b) contacting the first mixture with a second diluent under a second set of pre-determined conditions to obtain a second mixture, wherein the first diluent is microcrystalline cellulose, and wherein the second diluent is lactose monohydrate, and wherein the lactose monohydrate has a particle size in the range of 50 µm-600 µm; c) mixing the second mixture with the excipients disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the first diluent, second diluent, and the other excipients are sieved through a mesh screen of #16-#40 prior to the blending.

In an embodiment of the present disclosure, there is provided a dry process for preparation of pharmaceutical dosage form of vitamin K1 comprising: a) sieving a first diluent, second diluent, and the other excipients through a mesh screen of #16-#40; b) blending vitamin K1 with a first diluent at under a first set of pre-determined conditions to obtain a first mixture; c) contacting the first mixture with a second diluent under a second set of pre-determined conditions to obtain a second mixture; d) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1.

In an embodiment of the present disclosure, there is provided a dry process for preparation of pharmaceutical dosage form of vitamin K1 as described herein, wherein the process is performed under solvent (Aqueous and organic) free conditions.

In an embodiment of the present disclosure, there is provided a dry process for preparation of pharmaceutical dosage form of vitamin K1 comprising: a) blending vitamin K1 with a first diluent at under a first set of pre-determined conditions to obtain a first mixture; b) contacting the first mixture with a second diluent under a second set of pre-determined conditions to obtain a second mixture, wherein the first diluent is microcrystalline cellulose, and wherein the second diluent is lactose monohydrate; c) mixing the second mixture with the excipients selected from a group consisting disintegrant, lubricant and glidant under a third set of pre-determined conditions to obtain a third mixture; and d) compressing or encapsulating the third mixture to obtain the solid pharmaceutical dosage form of vitamin K1, wherein the process is performed under anhydrous conditions.

In an embodiment of the present disclosure, there is provided a dry process for preparation of pharmaceutical dosage form of vitamin K1 as described herein, wherein the at least one disintegrant is selected from a group consisting of starch, pre-gelatinized starch, partially pre-gelatinized starch, crospovidone, sodium starch glycolate, croscarmellose sodium, and hydroxypropyl cellulose; the lubricant(s) is at least one selected from a group consisting of magnesium stearate, calcium stearate, talc, and sodium stearyl fumarate; and the glidant(s) is at least one of silicon dioxide, talc and colloidal silicon dioxide.

In an embodiment of the present disclosure, there is provided a dry process for preparation of pharmaceutical dosage form of vitamin K1 comprising: a) blending vitamin K1 with a first diluent at under a first set of pre-determined conditions to obtain a first mixture; b) contacting the first mixture with a second diluent under a second set of pre-determined conditions to obtain a second mixture, wherein the first diluent is microcrystalline cellulose, and wherein the second diluent is lactose monohydrate; c) mixing the second mixture with the excipients selected from a group consisting of disintegrant, lubricant and glidant under a third set of pre-determined conditions to obtain a third mixture; and d) compressing or encapsulating the third mixture to obtain the solid pharmaceutical dosage form of vitamin K1, wherein the at least one disintegrant is selected from a group consisting of starch, pre-gelatinized starch, partially pre-gelatinized starch, crospovidone, sodium starch glycolate, croscarmellose sodium, and hydroxypropyl cellulose; the lubricant(s) is at least one selected from a group consisting of magnesium stearate, calcium stearate, talc, and sodium stearyl fumarate; and the glidant(s) is at least one of silicon dioxide, talc, and colloidal silicon dioxide.

In an embodiment of the present disclosure, there is provided a solid pharmaceutical dosage form as described herein, wherein the pharmaceutically administrable dosage form is in the form of tablets, powders, capsules, pellets, granules, and sachets.

In an embodiment of the present disclosure, the solid pharmaceutical dosage form as described herein is an immediate release solid oral dosage form.

In an embodiment of the present disclosure, there is provided a solid pharmaceutical dosage form of vitamin K1 vitamin comprising trans phytonadione having a weight percentage in a range of 80-98% with respect to the total eight diastereomers; cis phytonadione having a weight percentage in the range of 1-21% with respect to the total eight diastereomers, wherein the dosage form is substantially free (i.e. each isomer: NMT 0.15% w/w) of other six diastereomers of vitamin K1.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

EXAMPLES

The disclosure will now be illustrated with working examples, which is intended to illustrate the working of disclosure not intended to take restrictively to imply any limitations on the scope of the present disclosure. Unless defined otherwise, all technical and scientific terms used herein have the same meaning as commonly understood to any one of the ordinary skilled in the art to which this disclosure belongs. Although methods and materials similar or equivalent to those described herein can be used in the practice of disclosed methods and compositions, the exemplary methods, devices and materials are described herein. It is to be understood that this disclosure is not limited to particular methods, and experimental conditions described, as such methods and conditions may apply.

Example-1: Formulations

Two different solid dosage pharmaceutical forms, namely formulation A1 and A2 were prepared by mixing all the constituents of the formulation in appropriate weight percentages, as provided below in Table 1.

TABLE 1

| Item # | Constituents | A1 Amt. per tablet | A1 Wt. % | A2 Amt. per tablet | A2 Wt. % |
|---|---|---|---|---|---|
| 1 | Vitamin K1 | 5 | 3.70 | 5.00 | 3.85 |
| 2 | MCC and mannitol (Avicel HFE102) | 33.35 | 24.70 | 0 | 0 |
| 3 | Lactose monohydrate (supertab 30GR) | 77.84 | 57.66 | 102.25 | 78.65 |
| 4 | Pre-gelatinized starch | 13.50 | 10.00 | 3.25 | 2.50 |

TABLE 1-continued

| Item # | Constituents | A1 Amt. per tablet | A1 Wt. % | A2 Amt. per tablet | A2 Wt. % |
|---|---|---|---|---|---|
| 5 | Colloidal $SiO_2$ | 3.75 | 2.78 | 0.65 | 0.50 |
| 6 | Magnesium stearate NF | 1.56 | 1.16 | 1.30 | 1.00 |
| 7 | Dicalcium phosphate | 0 | 0 | 13 | 10 |
| 8 | Talc | 0 | 0 | 1.3 | 1 |
| 9 | Acacia | 0 | 0 | 3.25 | 2.5 |
| 10 | Total | 135.00 | 100 | 130 | 100 |
| | Physical parameters | | | | |
| 11 | Visual observation | Uniform appearance with no visual defects | | Drug Mottling - drug squeezed out and appear as contrasting spots on the surface due to non-homogeneity. | |
| 12 | Hardness | 3.5 kp | | 3.5 kp | |
| 13 | Disintegration time | 59 seconds | | 23 minutes | |
| 14 | Dissolution rate (0.1% HCL added with 0.1% triton X 100) | Not less than 85% of vitamin K1 was released in 15 mins. | | | |

Directly compressible grade of lactose monohydrate of (particle size of 50-600 μm) was utilized to get free flowing directly compressible blend of phytonadione.

TABLE 2

| Direct compressible grade particle size (50-600 μm) | Percentage of size Limit |
|---|---|
| <75 μm | 10-30% |
| <150 μm | 40-70% |
| <425 μm | 90-100% |
| <600 μm | ≥100% |

Example 2: Process of Preparing the Solid Dosage Pharmaceutical Forms of A1

The process for preparation of solid pharmaceutical dosage forms of formulation A1 comprises the steps of:

Step 1: Sift item #2 to Item #6 individually through 40# sieve;

Step 2: Load the sifted Item #2 in HSMG (High Shear Mixing Granulator) Bowl;

Step 3: Load phytonadione above Item #2 and mix by using HSMG (i.e. Mix for 10 mins at 230 RPM of Agitator) and discharge to obtain a first mixture;

Step 4: Co-Sift the first mixture along with item #3 through 40# sieve, to obtain a second mixture;

Step 5: Load the second mixture in V cone blender and Mix for 10 mins at 15 RPM;

Step 6: Load 40# sifted pregelatinized starch in V cone blender and mix for 5 mins at 15 RPM;

Step 7: Lubricate the blended material with 40# sifted magnesium stearate and 40# sifted colloidal silicon dioxide in V cone blender for 5 mins at 15 RPM to obtain a third mixture;

Step 8: Compress the final blend using suitable compression machine into tablet, to obtain the solid pharmaceutical dosage form of vitamin K1.

Example 3: Process of Preparing the Solid Dosage Pharmaceutical Forms of A2

Step 1: Sift Item #3 through 40# sieve and load it in HSMG (High Shear Mixing Granulator) bowl;
Step 2: Disperse vitamin K1 in Item #3 by using HSMG (i.e. Mix for 10 mins at 230 RPM of Agitator) to obtain a first mixture;
Step 3: Discharge the first mixture and co-Sift first mixture along with item #7 and item #9 through 40# sieve;
Step 4: Load the step 3 material in V cone blender and Mix for 10 mins at 15 rpm;
Step 5: Load pre-sifted (40#) pre-gelatinized starch, magnesium stearate, colloidal silicon dioxide and talc in V cone blender and mix for 5 mins at 15 rpm to obtain a third mixture.
Step 6: Compress the final blend using suitable compression machine into desired size/shape of tablet.

Advantages of the Present Disclosure

The present disclosure provides a blending vitamin K1 with a first diluent under a first set of pre-determined conditions to obtain a first mixture; contacting the first mixture with a second diluent under a second set of pre-determined conditions to obtain a second mixture; mixing the second mixture with the excipients of other category (disintegrant, lubricant and glidant etc) under a third set of pre-determined conditions to obtain a third mixture; and compressing or encapsulating the third mixture to obtain the solid pharmaceutical dosage form of vitamin K1. The solid pharmaceutical dosage forms of vitamin K1 does not contain dicalcium phosphate unlike the conventionally used formulations, thereby overcoming the challenges associated with the use of DCP. Also, the vitamin K1 synthesized by the process of the present disclosure is simple, does not require the use of solvents, energy, time or cost intensive processes, unlike the conventionally used processes.

We claim:
1. A dry process for preparing a solid pharmaceutical dosage form of vitamin K1 consisting of:
   a. blending vitamin K1 with a sifted first diluent for a period of 5-15 minutes at a speed of 200-350 rpm to obtain a first mixture, wherein the sifted first diluent is microcrystalline cellulose (MCC) and mannitol;
   b. co-sifting the first mixture with a second sifted diluent for a period of 5-15 minutes at a speed of 10-20 rpm to obtain a second mixture, wherein the second sifted diluent is lactose monohydrate;
   c. mixing the second mixture with a sifted excipient for a period of 5-15 minutes at a speed of 10-20 rpm to obtain a third mixture, wherein the excipient is pregelatinized starch; and
   d. compressing or encapsulating the third sifted mixture to obtain the solid pharmaceutical dosage form of vitamin K1 wherein the process is performed under solvent free condition.

2. The process as claimed in claim 1, wherein the process is carried out at a temperature range of 15-30° C., and a relative humidity limit in the range of 40-65%.

3. The process as claimed in claim 1, wherein the vitamin K1 to the first diluent weight ratio is in the range of to 1:200.

4. The process as claimed in claim 1, wherein the lactose monohydrate has a particle size in the range of 50 μm-600 μm.

5. The process as claimed in claim 1, wherein the first diluent, second diluent, and the excipient are sieved through a mesh screen size of #16-#40 prior to the blending.

6. The process as claimed in claim 1, wherein the vitamin K1 comprises trans phytonadione having a weight percentage in a range of 80-98% with respect to total eight diastereomers; the cis phytonadione having a weight percentage in the range of 1-21% with respect to the total eight diastereomers, wherein the dosage form is substantially free (i.e. each isomer: NMT 0.15% w/w) of other six diastereomers of vitamin K1.

* * * * *